(12) United States Patent
Endo et al.

(10) Patent No.: US 8,790,598 B2
(45) Date of Patent: Jul. 29, 2014

(54) REACTION CUVETTE FOR AUTOMATIC ANALYZER AND METHOD OF SURFACE TREATMENT FOR REACTION CUVETTE

(75) Inventors: Masashi Endo, Hitachinaka (JP); Hiroaki Ishizawa, Hitachinaka (JP); Hiroyuki Mishima, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 609 days.

(21) Appl. No.: 12/422,322

(22) Filed: Apr. 13, 2009

(65) Prior Publication Data

US 2009/0257918 A1    Oct. 15, 2009

(30) Foreign Application Priority Data

Apr. 15, 2008  (JP) ................. 2008-105230

(51) Int. Cl.
*B01L 3/14*    (2006.01)
(52) U.S. Cl.
USPC ........... 422/549; 422/547; 422/557; 422/558; 204/157.15; 204/157.4
(58) Field of Classification Search
USPC ................. 422/547, 548, 549, 556, 557, 558; 204/157.15, 157.4
See application file for complete search history.

(56) References Cited

U.S. PATENT DOCUMENTS

| | | | |
|---|---|---|---|
| 4,357,301 A | 11/1982 | Cassaday et al. | |
| 5,041,266 A | 8/1991 | Fox | |
| 5,419,872 A * | 5/1995 | Montgomery et al. | 422/549 |
| 2002/0170817 A1 * | 11/2002 | Goudy, Jr. | 204/164 |
| 2003/0064005 A1 | 4/2003 | Sasaki et al. | |
| 2004/0047762 A1 * | 3/2004 | Masaoka et al. | 422/22 |
| 2005/0047970 A1 | 3/2005 | Amo et al. | |
| 2008/0314167 A1 | 12/2008 | Kahl | |
| 2009/0029476 A1 | 1/2009 | Ishii | |

FOREIGN PATENT DOCUMENTS

| | | |
|---|---|---|
| EP | 0 290 125 A2 | 11/1988 |
| EP | 1 859 866 A1 | 11/2007 |
| EP | 1994988 A1 | 11/2008 |
| EP | 2 006 690 A2 | 12/2008 |
| EP | 2 008 715 A1 | 12/2008 |
| JP | 58-005656 | 1/1983 |
| JP | 63-134053 A | 6/1988 |
| JP | 05-269370 | 10/1993 |
| JP | 06-148184 | 5/1994 |

(Continued)

OTHER PUBLICATIONS

Certified translation of JP2007183240A.*

*Primary Examiner* — Jill Warden
*Assistant Examiner* — Dwayne K Handy
(74) *Attorney, Agent, or Firm* — Mattingly & Malur, PC (57) ABSTRACT

The present invention provides reaction cells capable of maintaining stable analytical performance by preventing bubble adhesion and reducing sample carryover even if the amount of sample liquid for a single test is further reduced in the future. The invention further provides an automatic analyzer that uses the reaction cells and a method for enhancing the hydrophilicity of the inner surfaces of the reaction cells. According to the invention, a reaction cell has a first electrode inserted thereinto and a second electrode disposed on the bottom side of the reaction cell. A voltage is applied between the first electrode and the second electrode to cause electric discharge between the electrodes. This allows for enhancing only the hydrophilicity of the bottom inner surface and the four bottom corners of the reaction cell to which large bubbles adhere easily.

7 Claims, 9 Drawing Sheets

(56) References Cited

FOREIGN PATENT DOCUMENTS

| JP | 2001-335946 A | 12/2001 |
| JP | 2003-020350 | 1/2003 |
| JP | 2005-77263 A | 3/2005 |
| JP | 2006-125897 A | 5/2006 |
| JP | 2007-089530 | 4/2007 |
| JP | 2007-134056 | 5/2007 |
| JP | 2007-183240 | 7/2007 |
| JP | 2007183240 A * | 7/2007 |
| JP | 2008-002850 | 1/2008 |
| JP | 2008-286539 A | 11/2008 |
| WO | 2007/116838 A1 | 10/2007 |

* cited by examiner

REACTION CUVETTE FOR AUTOMATIC ANALYZER AND METHOD OF SURFACE TREATMENT FOR REACTION CUVETTE

BACKGROUND OF THE INVENTION

1. Field of the Invention

The present invention relates to an automatic analyzer for performing qualitative/quantitative analysis of biological samples such as blood and urine. More particularly, the present invention relates to reaction cuvettes in which a biological sample reacts with reagents and to an automatic analyzer equipped with these reaction cuvettes.

2. Description of the Related Art

In the field of clinical testing, with the increase in the test selection to a sample, the sample volume required to a single test decreases. As a result, samples are routinely analyzed in very small amounts. If the sample quantity for a single analysis can be further reduced, the quantity of reagent required for a single analysis can also be reduced, leading to reduction in costs as well. In addition, the quantity of waste liquid resulting from the analysis can also be reduced.

Along with the reduction in sample volume, progress is made toward reduction of reaction cuvettes in size (the reaction cuvettes are hereinafter referred to as reaction cells). However, the size reduction of a reaction cell also leads to reduction in the area in the reaction cell passed by the light from the photometer. As a result, the presence of bubbles in reacted sample liquid now becomes problematic, which could have been ignored in the conventional automatic analyzers. To be more specific, when a photometric light beam is directed to bubbles in a reacting sample liquid, the bubbles diffuse the light beam, adversely affecting the photometric analysis. In some cases, the photometry analysis itself may not be done.

In order to solve the above problem, Japanese Unexamined Patent Application Publication No. 2005-77263 (Patent Document 1) proposes a method for making the status of an inner surface of a reaction cuvette hydrophilic with the use of ozone treatments.

In addition, Japanese Unexamined Patent Application Publication No. 2006-125897 (Patent Document 2) proposes a method for performing surface treatment to the area passed by the photometric light beam and its vicinity of a reaction cell so that the hydrophilic properties (wettability) of only those regions are increased.

SUMMARY OF THE INVENTION

When the status of the area passed by the photometric light beam and its vicinity of a reaction cell are turned to be hydrophilic, the number of bubbles adhering to those areas decreases. However, if a photometric area approaches non-photometric surfaces or the bottom of a reaction cell with the progress of the size reduction of reaction cells, bubbles adhering to the side and bottom surfaces of the reaction cell may interfere with the optical axis of a photometric beam.

An object of the present invention is thus to provide a reaction cell, even if reduced in size, immune to the influence of bubbles in a reacting sample liquid, and an automatic analyzer using these reaction cells.

The above object can be achieved by the following means:
1) a reaction cell whose corners at the inner bottom and side surfaces and inner side surfaces are treated to make their status hydrophilic; 2) a hydrophilicity-enhancing apparatus with a discharge electrode structure for generating a plasma and for making the corners status hydrophilic and the method for making the corners status hydrophilic.

In accordance with the present invention, even if the quantity of sample liquid for a single analysis is further reduced in the future, it is possible to prevent bubbles from adhering to an inner surface of a reaction cell and also to achieve highly reliability in photometry. Moreover, sample carryover, which is another problem upon the quantity reduction in sample liquid, can also be solved at the same time, contributing to improvements in accuracy of photometric analysis.

DESCRIPTION OF THE PREFERRED EMBODIMENTS

If the status of an inner surface of a reaction cell makes hydrophilic, adhesion of bubbles to the inner surface can be prevented, but at the same time, sample carryover may occur due to the tendency of the inner surface to attract water (sample liquid). Because the amount of sample carryover can be decreased by reducing the status of the area of an inner surface of the reaction cell turned to be hydrophilic, it is desirable that only a surface to which large bubbles adhere easily is turned to be hydrophilic.

Our study has revealed that surfaces to which small bubbles adhere easily are planar portions such as the area passed by the photometric light beam and side surfaces whereas surfaces to which large bubbles adhere easily are the inner bottom surface and the four bottom corners of a cell. A possible explanation is the following. A bubble changes its shape in such a way as to minimize its surface energy. The bubble stabilizes itself at a corner rather than at a planar portion because the bubble surface area is smaller (hence smaller surface energy) when the bubble adheres to the corner than to the planar portion.

In accordance with the present invention, therefore, the status of the inner bottom surface of a reaction cell, especially that of the corners at the inner bottom and side surfaces of the cell are turned to be hydrophilic intensively, unlike conventional hydrophilicity-enhancing treatments limited to the area passed by the photometric light beam.

In accordance with a hydrophilicity-enhancing treatment of the invention, a reaction cell has a first electrode inserted thereinto, a second electrode disposed bottom side of the reaction cell, and a third electrode that faces the outer surfaces of the reaction cell and is integrated to the second electrode. A voltage is applied between the first electrode and the integrated two electrodes, to cause discharge between the first electrode and the integrated two electrodes in order to generate plasma between the first electrode and the integrated two electrodes.

In addition to the third electrode that faces the outer surfaces of the reaction cell, the second electrode is also provided on the bottom side of the reaction cell. As a result, electricity is discharged toward the outer bottom surface of the reaction cell as well. This makes it possible to make the status of the inner bottom surface of the reaction cell hydrophilic.

Moreover, the area whose status is turned to be hydrophilic can be reduced by reducing the height of the third electrode facing the outer surfaces of the reaction cell or by excluding the third electrode.

If the amount of sample carryover is to be reduced by further reducing the area whose status is tuned to be hydrophilic, the second electrode is shaped to have five protrusions, one being disposed below the center of the inner bottom surface of the reaction cell, four being disposed at the each four corners of the inner bottom surface of the reaction. Alternatively, the first electrode or the second electrode is partially covered with insulating materials.

By exploiting the tendency of electricity to be discharged intensively toward projected portions of an object, the area whose status is turned to be made hydrophilic can be limited only to the inner bottom surface and the four corners of the reaction cell to which bubbles adhere easily.

Embodiments of the present invention are described below with reference to the accompanying drawings.

First Embodiment

Figure 1:
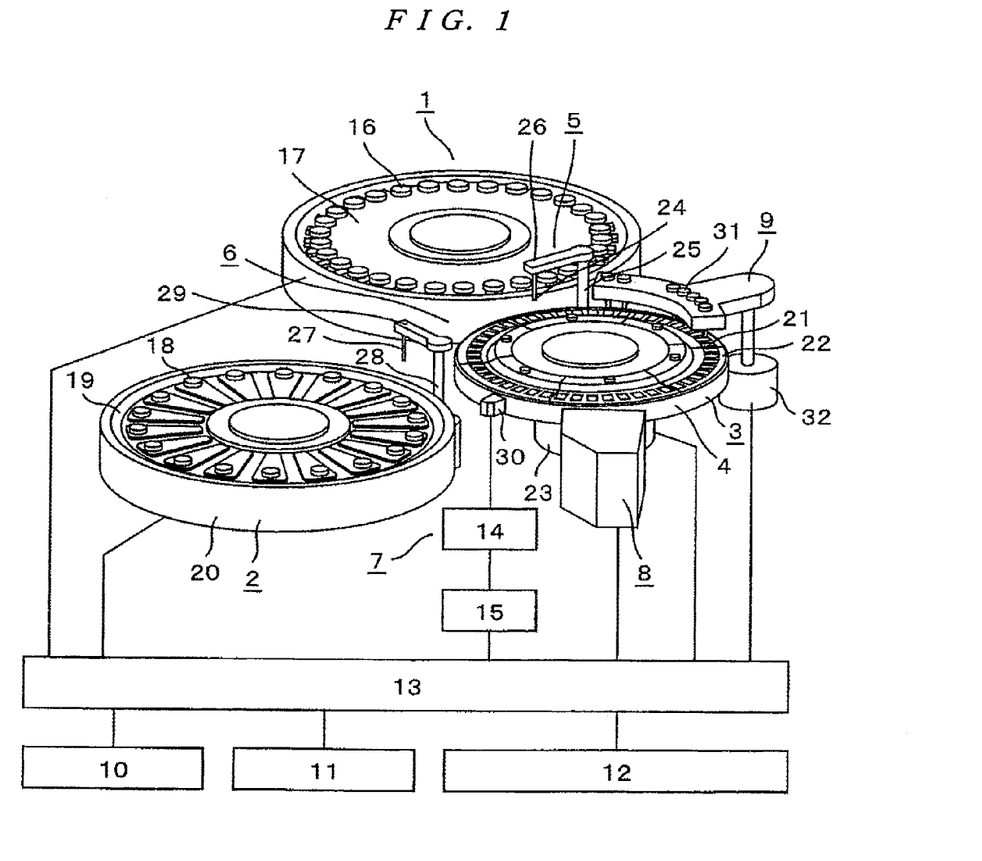
FIG. 1 is a perspective view illustrating the configuration of an automatic analyzer according to an embodiment of the present invention.

With reference to FIG. 1, an automatic analyzer according to a first embodiment mainly includes a sample disk 1, a reagent disk 2, a reaction disk 3, a reaction bath 4, a sampling mechanism 5, a pipetting mechanism 6, a stirring mechanism 7, a photometric mechanism 8, a rinsing mechanism 9, a display unit 10, an input unit 11, a storage unit 12, and a control unit 13.

In FIG. 1, segments composed of multiple sample cuvettes 16 filled with collected samples are fixedly arrayed along the circumference of a circular disk 17 on the sample disk 1. A drive mechanism including a motor and a rotary shaft, which are not illustrated, can rotate the circular disk 17 to the certain positions.

Multiple reagent bottles 18, which are filled with reagents to be mixed and reacted with a sample, are fixedly arrayed along the circumference of a circular disk 19 on the reagent disk 2. The circular disk 19 is surrounded by a temperature-controlled cold reservoir 20. In addition, a drive mechanism including a motor and a rotary shaft, which are not illustrated, can rotate the circular disk 19 to the certain positions.

Multiple reaction cell holders 22, each of which holds some reaction cells 21 into which a sample and a reagent are dispensed, are mounted on the reaction disk 3. A drive mechanism 23 intermittently transfers the reaction cells 21 by constant cycle repeating rotational movement and stop motion alternately.

With continued reference to FIG. 1, the reaction bath 4 is disposed along the move path of the reaction cells 21. The reaction bath 4 is a thermostatic tank that controls mixed liquid (sample-reagent mixtures) in the reaction cells 21 keeping a particular temperature with the use of, for example, thermostatically controlled water in order to accelerate the chemical reaction of the mixed liquid. The reaction cells 21 move inside the reaction bath 4.

The sampling mechanism 5 includes, as shown in FIG. 1, a probe 24; an arm 26 attached to a support shaft 25; and a drive mechanism capable of reciprocating the arm 26 between the sample disk 1 and the reaction disk 3 around the support shaft 25. According to a predetermined sequence, the sampling mechanism 5 dispenses a sample contained in one of the sample cuvettes 16 that is transferred to a particular position by the rotation of the sample disk 1 into one of the reaction cell 21. Likewise, the pipetting mechanism 6 includes a probe 27; an arm 29 mounted on a support shaft 28; and a drive mechanism capable of reciprocating the arm 29 between the reagent disk 2 and the reaction disk 3 around the support shaft 28. According to a predetermined sequence, the pipetting mechanism 6 dispenses a reagent contained in one of the reagent bottles 18 that is transferred to a particular position by the rotation of the reagent disk 2 into one of the reaction cells 21. It should be noted that each of the sample cuvettes 16 contains various types of sample. Likewise, each of the reagent bottles 18 contains various types of reagent. These samples and reagents are dispensed into the reaction cells 21 as much as needed.

The stirring mechanism 7 is a noncontact-type stirring mechanism. When a reaction cell 21 is transferred to a stirring position, the stirring mechanism 7 radiates sound waves toward a side surface of the reaction cell 21, thereby mixing the sample and reagent inside the reaction cell 21. The stirring mechanism 7 includes a fixed unit 30 secured at a position that allows the stirring mechanism 7 to radiate sound waves toward a side surface of a reaction cell 21 at the stirring position; a piezoelectric element driver 14 for driving a piezoelectric element; and a stirring mechanism controller 15. The stirring mechanism controller 15 is connected to the control unit 13, drives the piezoelectric element driver 14, and controls the entire stirring mechanism 7.

Although not illustrated in FIG. 1, the photometric mechanism 8 includes a light source, a photometer, a lens, and a photometric-signal processor. The photometric mechanism 8 uses light to measure the properties of a sample such as the absorbance of mixed liquid contained in a reaction cell 21. The rinsing mechanism 9 includes Multiple nozzles 31 and a vertical drive mechanism 32 for vertically moving the nozzles 31. The rinsing mechanism 9 aspirates the reacted liquid from a reaction cell 21 that has been transferred to a rinsing position and then discharges cleaning liquid into the reaction cell 21 to rinse it.

The display unit 10 displays various kinds of information such as analysis item and analysis result information, and the input unit 11 inputs various kinds of information such as analysis item information. Further, the storage unit 12 stores various kinds of information including predetermined sequences (programs) for controlling various mechanisms, analysis item information, and the like.

In addition to the above-described components, the automatic analyzer according to the present embodiment further includes a syringe, a pump, and the like. The control unit 13 controls all the components including those described above according to a sequence stored in the storage unit 12.

Discussed next is the operation of the thus-configured automatic analyzer.

When a reaction cell 21 rinsed by the rinsing mechanism 9 is transferred to a sample dispensing position on the reaction disk 3 by the rotation of the reaction disk 3, the sample disk 1 also rotates so that a sample cuvette 16 containing a sample therein is transferred to a sampling position on the sample disk 1. Likewise, the reagent disk 2 rotates so that a particular reagent bottle 18 is transferred to a pipetting position on the reagent disk 2.

Subsequently, the sampling mechanism 5 operates to dispense the sample contained in the sample cuvette 16 transformed to the sampling position into the reaction cell 21 transformed the sample dispensing position with the use of the probe 24. The reaction cell 21 into which the sample has been dispensed is then transferred to a reagent dispensing position on the reaction disk 3. Thereafter, the pipetting mechanism 6 operates to dispense the reagent contained in the reagent bottle 18 transformed to the pipetting position on the reagent disk 2 into the reaction cell 21 transformed to the reagent dispensing position.

The reaction cell 21 is then transferred to a stirring position, where the stirring mechanism 7 stirs the sample and the reagent.

The mixed liquid that completed the stirring is measured in terms of absorbance by the photometric mechanism 8 when the reaction cell 21 that contains the mixed liquid passes the area located between the light source and the photometer. This measurement is carried out over several cycles. After the measurement, the reaction cell 21 is rinsed by the rinsing mechanism 9.

Analysis with use of the automatic analyzer of the present embodiment is implemented by the above sequence of operations being performed also on the other reaction cells 21.

With now reference to FIGS. 2 through 9, the distinctive features of the present embodiment regarding a method for manufacturing the reaction cells 21 are described. Specifically, the present embodiment relates to a method of surface treatment for molded reaction cells 21.

Figure 2:
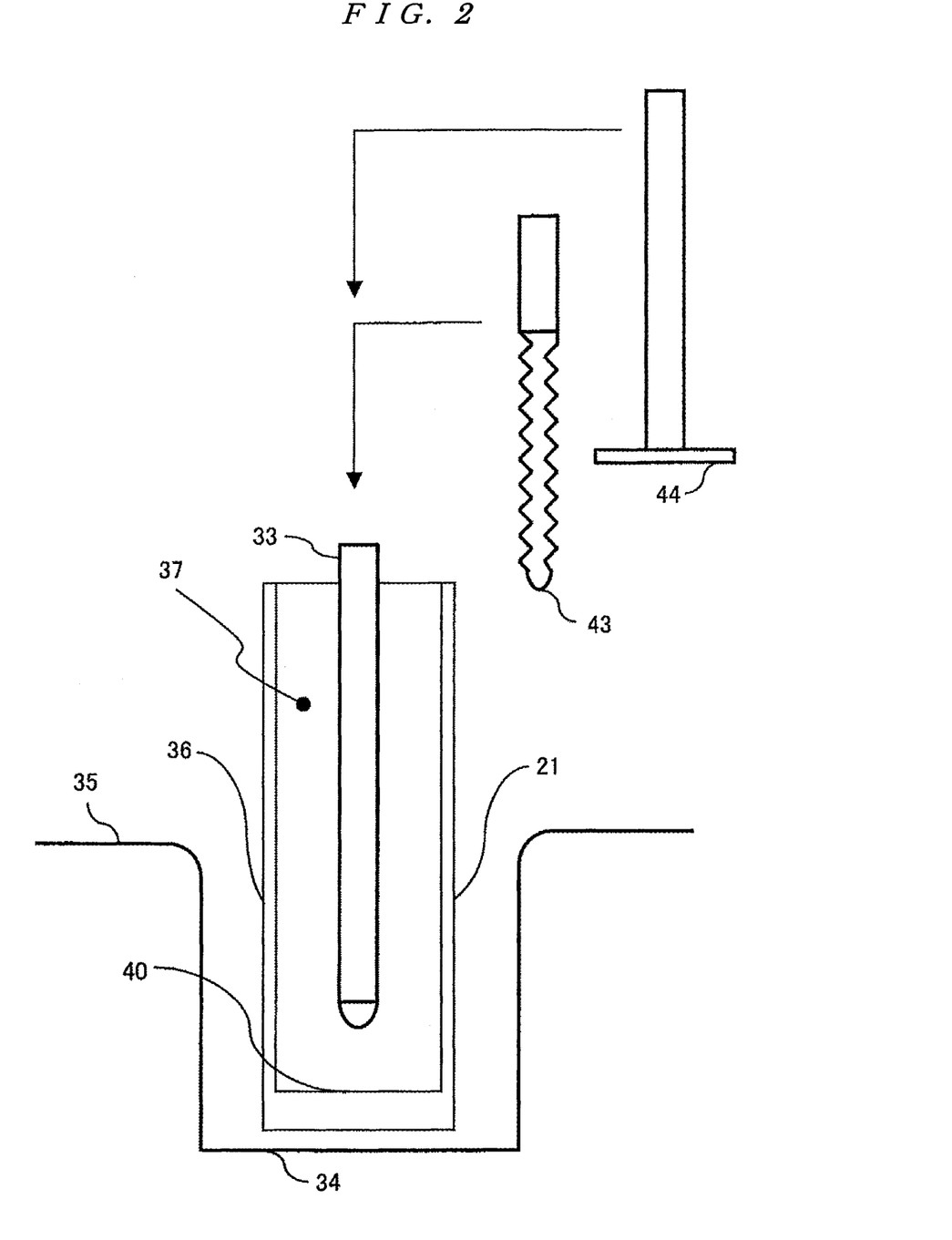
FIG. 2 is electrode configuration diagram 1 illustrating a first embodiment of the present invention.

FIG. 2 shows an example of the surface treatment in which not only the surface passed by the photometric light 36 of a reaction cell 21 but the inner bottom surface thereof whose status is turned to be hydrophilic.

A first electrode 33 is inserted into the reaction cell 21. A second electrode 34 is disposed on the bottom side of the reaction cell 21. A third electrode 35 faces the outer surfaces of the reaction cell 21. The second electrode 34 and the third electrode 35 are integrally molded. The first electrode 33 is connected to the high-voltage side of a high-voltage power supply unit whereas the second electrode 34 and the third electrode 35 are grounded. A voltage is applied between the first electrode 33 and the integrated two electrodes 34 and 35, to cause electric discharge between the electrodes. With the use of highly reactive radicals such as active oxygen species generated by the electric discharge, hydrophilicity is imparted to the inner bottom surface 40 and the surface passed by the photometric light 36 of the reaction cell 21.

If the hydrophilicity of the inner bottom surface 40 of the reaction cell 21 is necessary to be increased further, a first electrode 44 with a rectangular bottom surface at its bottom end, as shown in FIG. 2, may also be used.

Alternatively, a helix-shaped first electrode 43 can also be used for the purpose of obtaining stable electric discharge. In addition, a hollow first electrode having an opening may also be used to introduce noble gas thereto.

If the status of areas not desired are turned to be hydrophilic, which may lead to variations in product quality, the above hollow first electrode having an opening is preferably used to accurately impart local hydrophilicity in the reaction cell 21 by discharging ozone out of the reaction cell 21 with the aid of a aspirating device and by introducing inert gas into the reaction cell 21.

Figure 3:
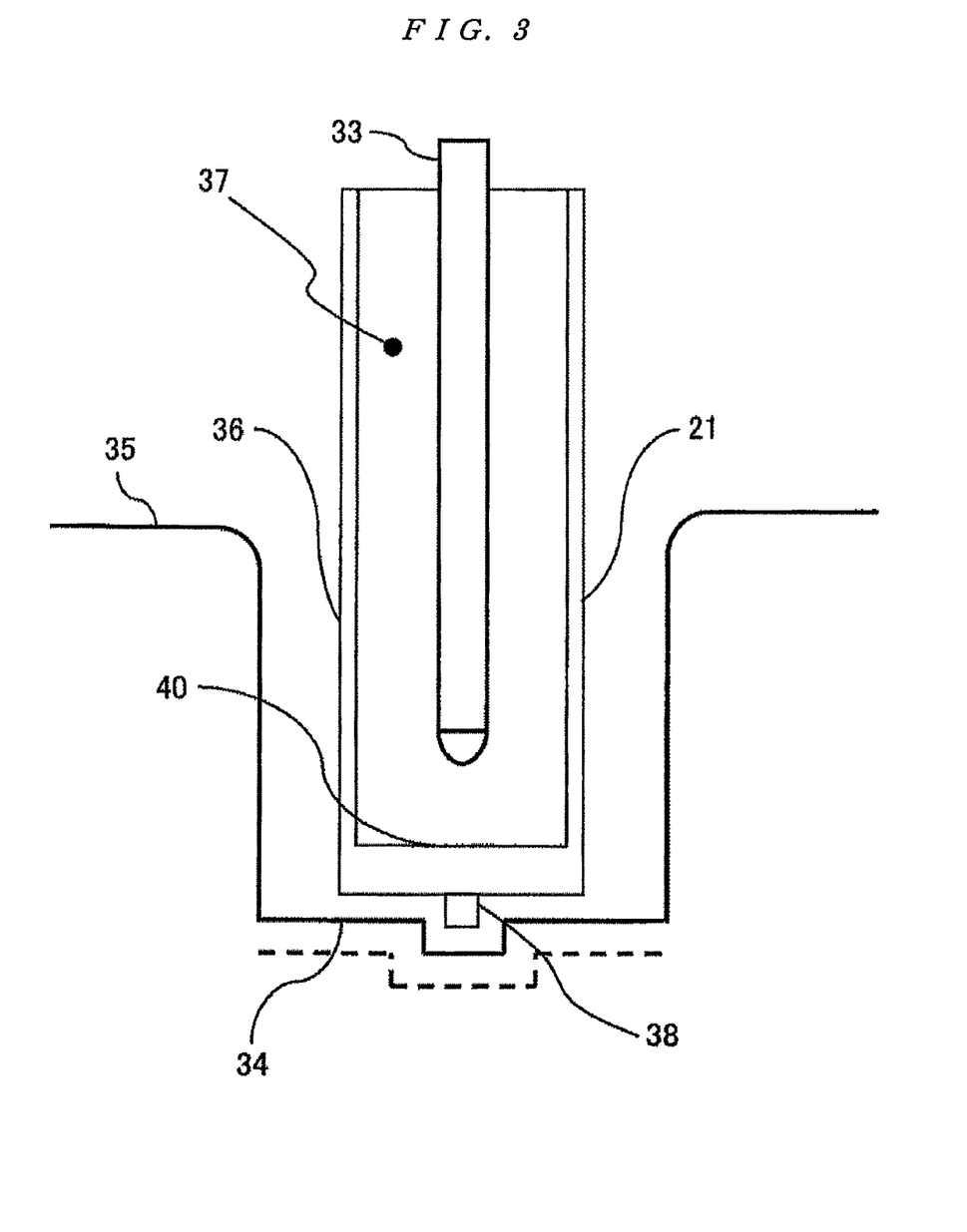
FIG. 3 is electrode configuration diagram 2 illustrating the first embodiment of the present invention.

If there exists a protrusion 38 on the outer bottom surface of the reaction cell 21 or if the outer bottom surface of the reaction cell 21 is not a simple plane, as shown in FIG. 3, the surface of the second electrode 34 may be shaped to have the same surface pattern as that of the outer bottom surface of the reaction cell 21.

Figure 4:
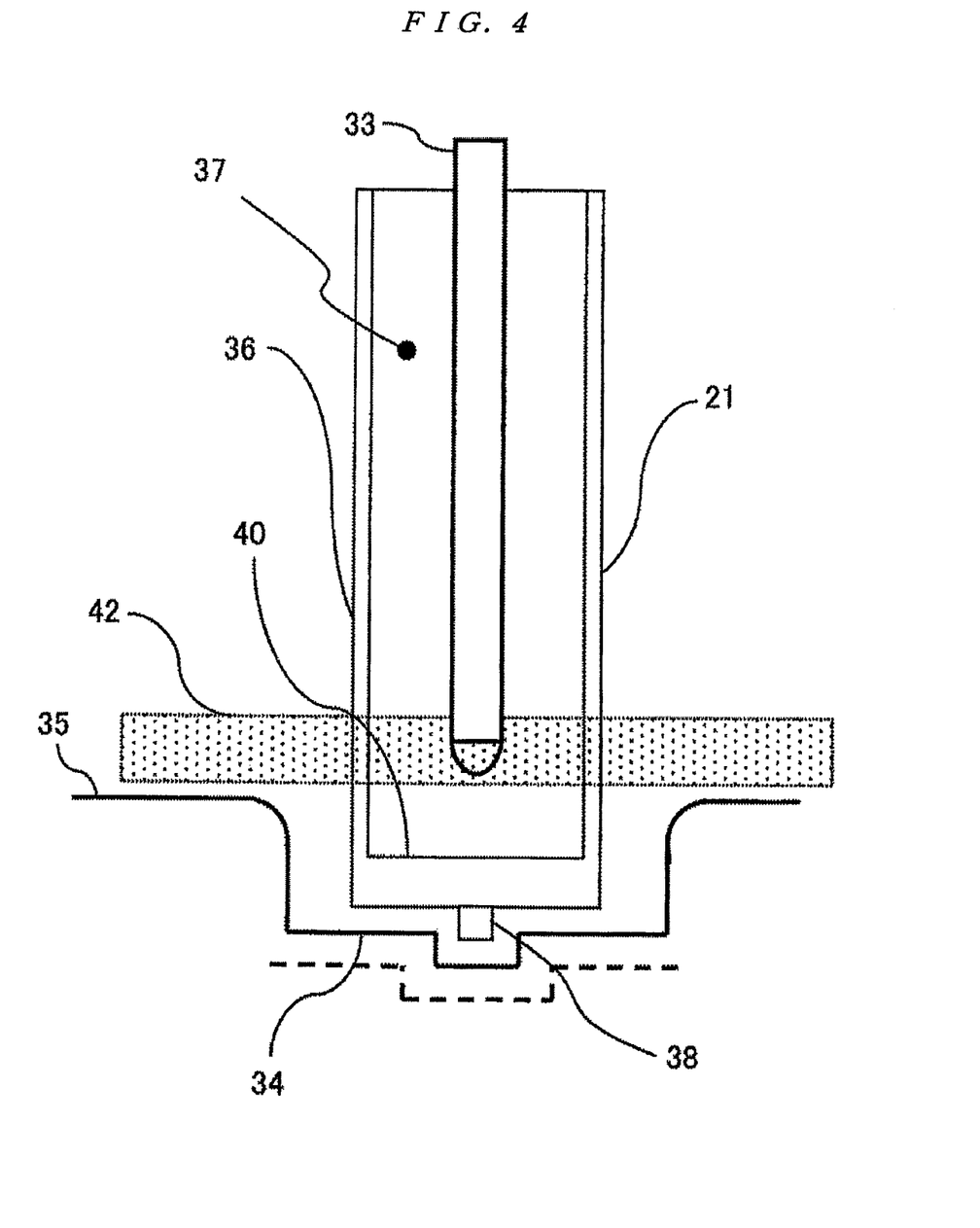
FIG. 4 is electrode configuration diagram 3 illustrating the first embodiment of the present invention.

As shown in FIG. 4, if the area whose status is turned to be hydrophilic is necessary to be reduced for the purpose of reducing the amount of sample carryover, the height of the third electrode 35 that faces the reaction cell 21 may be reduced so that the third electrode 35 is lower than the lower end of a photometric range 42.

Second Embodiment

Figure 5A:
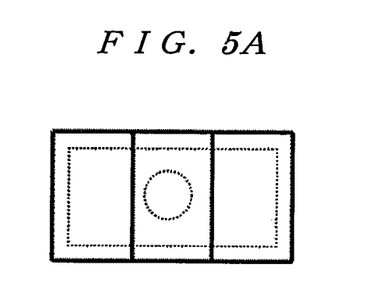
FIG. 5A shows a top surface of a second electrode.
Figure 5B:
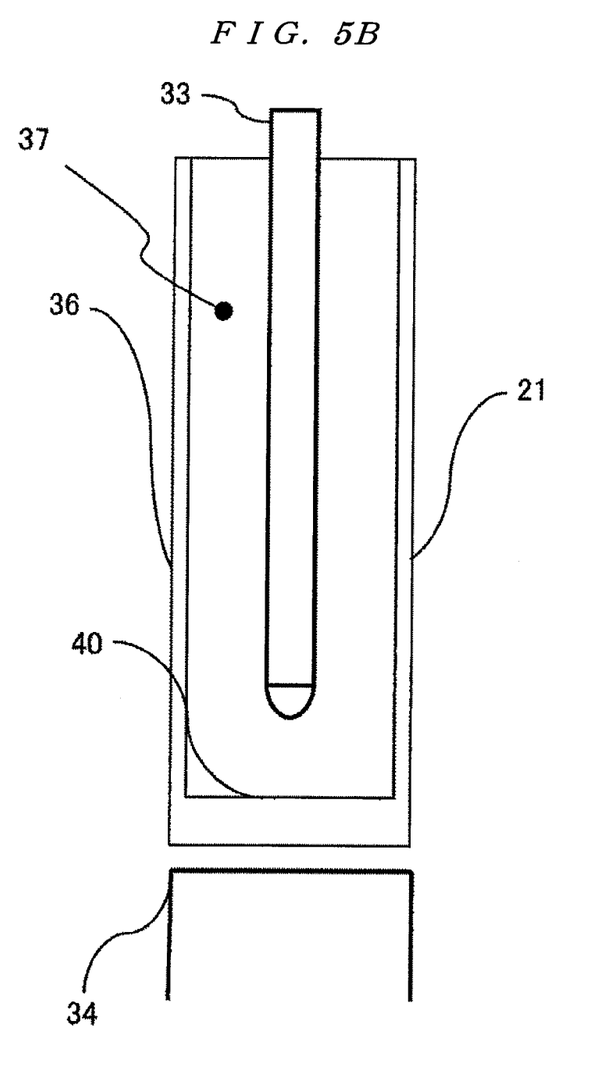
FIG. 5B is electrode configuration diagram 1 illustrating a second embodiment of the present invention.

FIGS. 5A and 5B show an example in which the third electrode 35 facing the reaction cell 21 is excluded.

The first electrode 33 is inserted into the reaction cell 21. The second electrode 34 is disposed on the bottom side of the reaction cell 21. The first electrode 33 is connected to the high-voltage side of a high-voltage power supply unit whereas the second electrode 34 is grounded. A voltage is applied between the first electrode 33 and the second electrode 34 to cause electric discharge between the electrodes. With the use of highly reactive radicals such as active oxygen species generated by the electric discharge, hydrophilicity is imparted only to the inner bottom surface 40 of the reaction cell 21 by oxidizing the inner bottom surface 40.

Since electricity tends to be discharged intensively toward projected portions of an object, high hydrophilicity is imparted to the four corners of the inner bottom surface 40. If uniform hydrophilicity is to be imparted, then, the area of the second electrode 34 facing the outer bottom surface of the reaction cell 21 is increased sufficiently relative to the first electrode 34, thereby discharging electricity toward portions of the outer bottom surface other than the four corner portions.

In addition, by exploiting the above-mentioned tendency of electric discharge, the corner potions of the second electrode 34 is located at desired positions, and hydrophilicity can be intentionally imparted only to desired portions of the reaction cell 21.

Figure 6A:
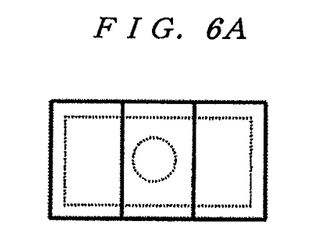
FIG. 6A shows a top surface of a second electrode.
Figure 6B:
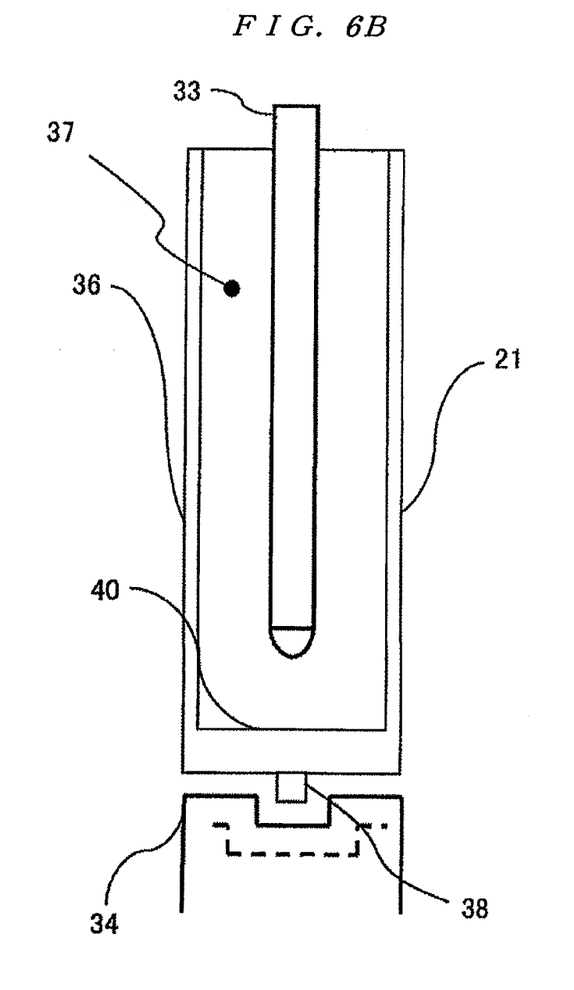
FIG. 6B is electrode configuration diagram 2 illustrating the second embodiment of the present invention.

If there exists the protrusion 38 on the outer bottom surface of the reaction cell 21 or if the outer bottom surface of the reaction cell 21 is not a simple plane, as shown in FIGS. 6A and 6B, the surface of the second electrode 34 may be shaped to have the same surface pattern as that of the outer bottom surface of the reaction cell 21.

Third Embodiment

Figure 7A:
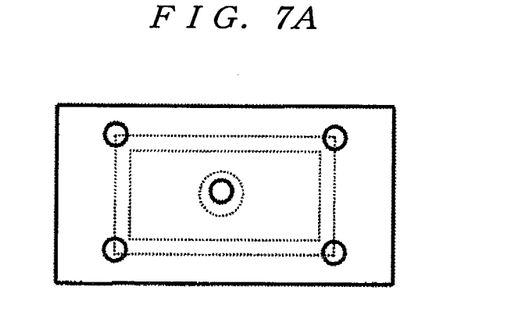
FIG. 7A shows a top surface of a second electrode.
Figure 7B:
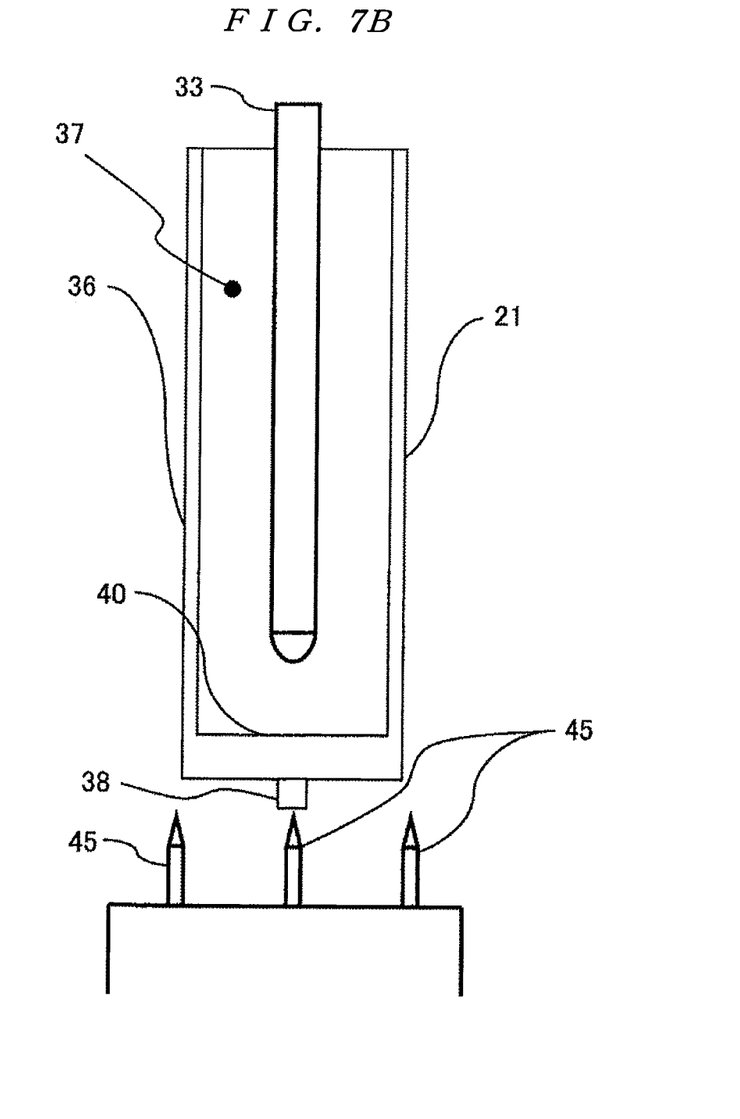
FIG. 7B is an electrode configuration diagram illustrating a third embodiment of the present invention.

FIGS. 7A and 7B show an example of the reaction cell 21 whose status inside is turned to be locally hydrophilic. The first electrode 33 is inserted into the reaction cell 21. Second electrodes 45 are disposed on the bottom side of the reaction cell 21. Each of the second electrodes 45 is sharply pointed and disposed on the extended line from the line that connects the lower end of the first electrode 33 and the target area of hydrophilicity. The first electrode 33 is connected to the high-voltage side of a high-voltage power supply unit whereas the second electrodes 45, which are disposed on the bottom side of the reaction cell 21, are grounded. A voltage is applied between the first electrode 33 and the second electrodes 45 to cause electric discharge between the electrodes. With the use of highly reactive radicals such as active oxygen species generated by the electric discharge, hydrophilicity is imparted to desired portions of the reaction cell 21.

If only large bubbles are necessary to be prevented from adhering to the inner surfaces of the reaction cell 21, four of the sharply-pointed second electrodes 45 are disposed each on the extended line from the line that connects the lower end of the first electrode 33 and one of the four bottom corners of the reaction cell 21 so that only the status of the four bottom corners can be turned to be hydrophilic.

Because large bubbles may adhere to a central portion of the reaction cell bottom 40 depending on the internal shape of the reaction cell bottom 40, one of the sharply-pointed second electrodes 45 can also be disposed on the bottom side of the central portion so that the status of the central portion of the reaction cell bottom 40 is turned to be hydrophilic.

Fourth Embodiment

Figure 8A:
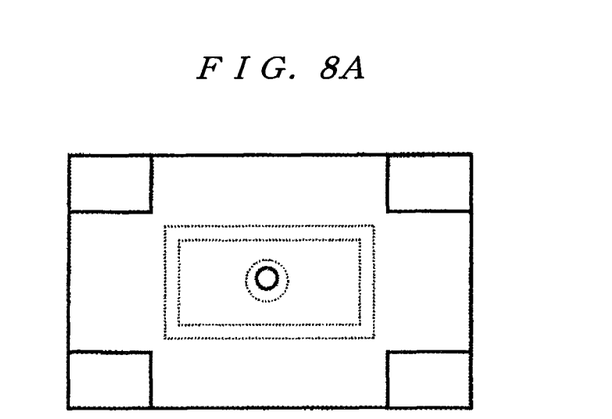
FIG. 8A shows a top surface of a second electrode.
Figure 8B:
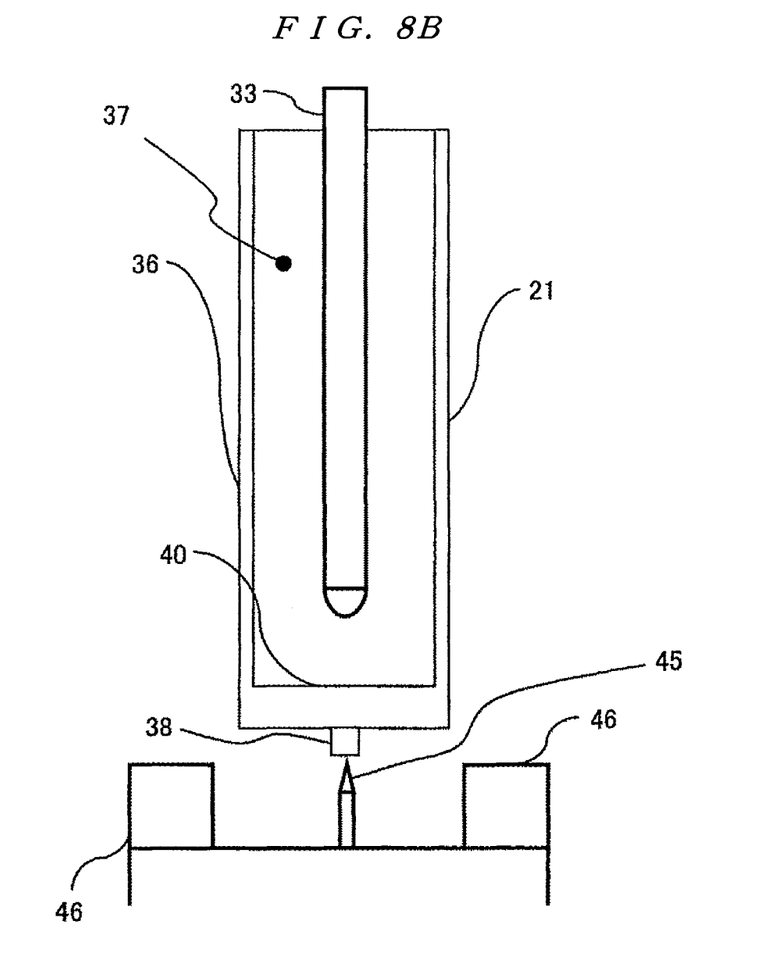
FIG. 8B is an electrode configuration diagram illustrating a fourth embodiment of the present invention.

FIGS. 8A and 8B show another example in which the reaction cell 21 whose status inside is turned to be locally hydrophilic. The first electrode 33 is inserted into the reaction cell 21. Second electrodes 46 are disposed on the bottom side of the reaction cell 21. Each of the second electrodes 46 is quadrangular in shape and disposed such that a corner of each of the second electrode 46 is on the extended line from the line that connects the lower end of the first electrode 33 and the target area of hydrophilicity. The first electrode 33 is connected to the high-voltage side of a high-voltage power supply unit whereas the second electrodes 46, which are disposed on the bottom side of the reaction cell 21, are grounded. A voltage is applied between the first electrode 33 and the second electrodes 46 to cause electric discharge between the electrodes. Hydrophilicity is imparted with the use of highly reactive radicals such as active oxygen species generated by the electric discharge.

If only large bubbles are to be prevented from adhering to the inner surfaces of the reaction cell 21, four of the quadrangular second electrodes 46 are disposed such that a corner of each of the four second electrodes 46 is on the extended line from the line that connects the lower end of the first electrode 33 and one of the four bottom corners of the reaction cell 21 so that only the status of the four bottom corners can be turned to be hydrophilic.

Because large bubbles may adhere to a central portion of the reaction cell bottom 40 depending on the internal shape of the reaction cell bottom 40, a second electrodes 45 can also be disposed on the bottom side of the central portion so that the status of the central portion of the reaction cell bottom 40 is turned to be hydrophilic.

Fifth Embodiment

Figure 9A:
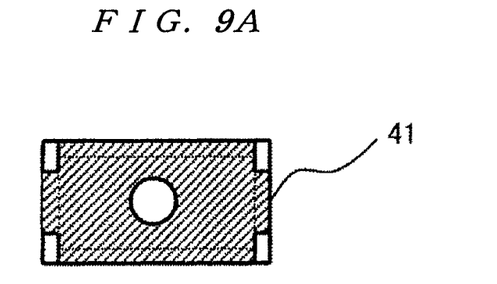
FIG. 9A shows a top surface of a second electrode.
Figure 9B:
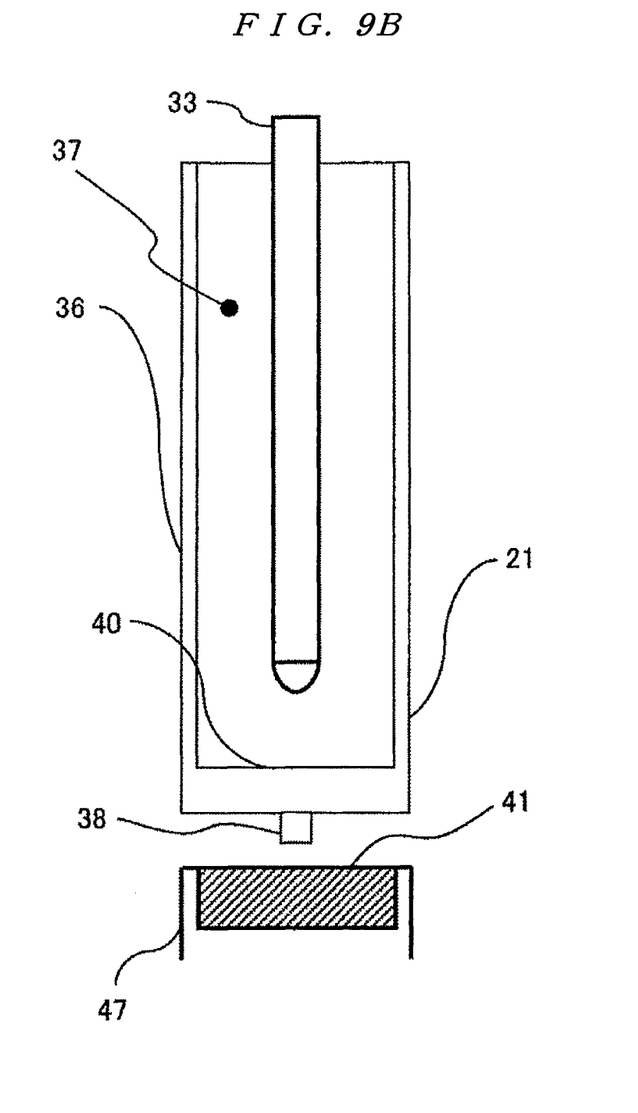
FIG. 9B is an electrode configuration diagram illustrating a fifth embodiment of the present invention.

FIGS. 9A and 9B show still another example of the reaction cell 21 whose status inside is turned to be locally hydrophilic. The first electrode 33 is inserted into the reaction cell 21. A second electrode 47 is disposed on the bottom side of the reaction cell 21. A particular portion of the second electrode 47 to avoid hydrophilicity is covered with an insulating material 41. The first electrode 33 is connected to the high-voltage side of a high-voltage power supply unit whereas the second electrode 47 facing the reaction cell bottom 40 is grounded. A voltage is applied between the first electrode 33 and the second electrode 47 to cause electric discharge between the electrodes. Hydrophilicity is imparted with the use of highly reactive radicals such as active oxygen species generated by the electric discharge.

If only large bubbles are to be prevented from adhering to the inner surfaces of the reaction cell 21, the entire surface of the second electrode 47 is covered with the insulating material 41 except four areas thereof that each exist on the extended line from the line that connects the lower end of the first electrode 33 and one of the four bottom corners of the reaction cell 21 so that only the status of the four bottom corners can be turned to be hydrophilic.

What is claimed is:

1. A method for manufacturing a reaction cell for use in an automatic analyzer, the method comprising:
    inserting a first electrode into the inside of said reaction cell;
    arranging a plurality of second electrodes with respect to said reaction cell at an outer bottom side of said reaction cell, each of said second electrodes having a protrusion;
    providing a bottom portion of said reaction cell that is rectangular shaped with four corners, and disposing each of said second electrodes corresponding to one of said four corners, respectively;
    arranging portions of said reaction cell to be made hydrophilic on a straight line extending from a distal end of said first electrode toward a distal end of said protrusion of respective ones of said second electrodes; and
    applying a voltage between said first electrode and said second electrodes to generate plasma discharge.

2. A method for manufacturing a reaction cell for use in an automatic analyzer, said method comprising:
    inserting a first electrode into the inside of said reaction cell;
    arranging a plurality of second electrodes with respect to said reaction cell, where said second electrodes are quadrangular;
    providing a bottom portion of said reaction cell that is rectangular shaped with four corners and disposing each of said second electrodes at an outer bottom side of said reaction cell corresponding to one of said four corners, respectively;
    arranging portions of said reaction cell to be made hydrophilic on a straight line extending from a distal end of said first electrode toward a corner portion of respective ones of said second electrodes; and
    applying a voltage between said first electrode and said second electrodes to generate plasma discharge.

3. A method for manufacturing a reaction cell for use in an automatic analyzer, said method comprising:
    inserting a first electrode into the inside of said reaction cell;
    arranging a plurality of second electrodes with respect to said reaction cell;
    providing a bottom portion of said reaction cell that is rectangular shaped with four corners;
    covering part of each of said second electrodes with an insulating material and leaving at least one area of each of said second electrodes exposed with respect to said insulating material,
    arranging each of said exposed areas of said second electrodes at an outer bottom side of said reaction cell corresponding to one of said four corners, respectively;
    arranging portions of said reaction cell to be made hydrophilic on a straight line extended from a distal end of said first electrode towards respective exposed areas of said second electrodes; and
    applying a voltage between said first electrode and said second electrodes to generate plasma discharge.

4. The method for manufacturing a reaction cell according to claim 1, wherein an additional protrusion is disposed below the center of an inner bottom surface of the reaction cell and substantially perpendicular to the inner bottom surface of the reaction cell.

5. The method for manufacturing a reaction cell according to claim 2, wherein the first electrode or the second electrodes are partially covered with an insulating material.

6. The method for manufacturing a reaction cell according to claim 1, wherein at least a horizontal cross-section of the lower end of the first electrode is rectangular.

7. The method for manufacturing a reaction cell according to claim 1, wherein the first electrode includes a helix-shaped protrusion.

* * * * *